US012796978B2

(12) United States Patent
Cleek et al.

(10) Patent No.: US 12,796,978 B2
(45) Date of Patent: Nov. 17, 2026

(54) STABILIZED MEDICAL DEVICES AND ASSOCIATED METHODS

(71) Applicant: W. L. Gore & Associates, Inc., Newark, DE (US)

(72) Inventors: Robert L. Cleek, Flagstaff, AZ (US); Peter D. Traylor, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1145 days.

(21) Appl. No.: 17/611,256

(22) PCT Filed: May 22, 2020

(86) PCT No.: PCT/US2020/034279
§ 371 (c)(1),
(2) Date: Nov. 15, 2021

(87) PCT Pub. No.: WO2020/242967
PCT Pub. Date: Dec. 3, 2020

(65) Prior Publication Data
US 2022/0225911 A1 Jul. 21, 2022

Related U.S. Application Data

(60) Provisional application No. 62/853,499, filed on May 28, 2019.

(51) Int. Cl.
*A61B 5/1486* (2006.01)
*A61B 5/145* (2006.01)

(52) U.S. Cl.
CPC ...... *A61B 5/14865* (2013.01); *A61B 5/14532* (2013.01); *A61B 2562/125* (2013.01)

(58) Field of Classification Search
CPC ............ A61B 5/14865; A61B 5/14532; A61B 2562/125
See application file for complete search history.

(56) References Cited

U.S. PATENT DOCUMENTS 6,187,555 B1 * 2/2001 Tautvydas ................. A61L 2/07 435/243
8,021,677 B2 9/2011 Cleek et al.
(Continued)

FOREIGN PATENT DOCUMENTS

CN 101133162 A 2/2008
CN 101909666 A 12/2010
(Continued)

OTHER PUBLICATIONS

Sekisui Diagnostics Glucose Oxidase L150 Sales Sheet May 2017 (Year: 2017).*
(Continued)

*Primary Examiner* — Christian Jang

(57) ABSTRACT

The present disclosure relates generally to stabilized medical devices having immobilized biologically active entities necessary for sterilization. The present disclosure provides a substrate (200) that is at least partially electrically conductive, and a stabilized enzyme layer (220) disposed over at least a portion of a surface of the substrate. The stabilized enzyme layer (220) may include at least one biologically active sensing component (240), such as glucose oxidase in the case of glucose sensors, and at least one stabilizing component (260) non-covalently combined with the biologically active sensing component (240). The present disclosure further provides the biologically active sensing component (240) having a biological activity detection level from about 25 U/cm3 to about 1,000,000 11/cm3 of the substrate following ethylene oxide sterilization of the biologically active sensing component. The present disclosure further provides methods of making stabilized medical devices having immobilized biologically active entities.

6 Claims, 13 Drawing Sheets

(56) References Cited

U.S. PATENT DOCUMENTS

| | | | | |
|---|---|---|---|---|
| 8,496,953 | B2 | 7/2013 | Cleek et al. | |
| 8,591,932 | B2 | 11/2013 | Cleek et al. | |
| 9,788,766 | B2 | 10/2017 | Simpson et al. | |
| 2006/0257996 | A1* | 11/2006 | Simpson | A61B 5/14865 435/287.2 |
| 2007/0111196 | A1* | 5/2007 | Alarcon | A61L 2/022 435/4 |
| 2007/0264301 | A1 | 11/2007 | Cleek et al. | |
| 2008/0003628 | A1 | 1/2008 | Kitabayashi et al. | |
| 2008/0089919 | A1 | 4/2008 | Cleek et al. | |
| 2008/0279909 | A1 | 11/2008 | Cleek et al. | |
| 2010/0285084 | A1 | 11/2010 | Yang et al. | |
| 2012/0138484 | A1 | 6/2012 | Bommakanti et al. | |
| 2012/0276565 | A1 | 11/2012 | Roedel et al. | |
| 2012/0283537 | A1 | 11/2012 | Petisce et al. | |
| 2015/0064228 | A1* | 3/2015 | Iwasaki | A61P 43/00 424/572 |
| 2015/0122647 | A1* | 5/2015 | Shah | G01N 27/3271 427/2.12 |
| 2016/0186230 | A1 | 6/2016 | Kaneda | |
| 2018/0204137 | A1 | 7/2018 | Margraf et al. | |
| 2019/0249214 | A1 | 8/2019 | Chu et al. | |

FOREIGN PATENT DOCUMENTS

| | | | |
|---|---|---|---|
| CN | 102712946 | A | 10/2012 |
| CN | 104031151 | A | 9/2014 |
| CN | 106929500 | A | 7/2017 |
| EP | 2023967 | B1 | 3/2017 |
| JP | 08-005601 | A | 1/1996 |
| JP | 2008-154573 | A | 7/2008 |
| JP | 2009-545333 | A | 12/2009 |
| JP | 2016-121989 | A | 7/2016 |
| WO | 2007/133699 | A2 | 11/2007 |

OTHER PUBLICATIONS

Sola-Penna et al. "Stabilization against Thermal Inactivation Promoted by Sugars on Enzyme Structure and Function: Why Is Trehalose More Effective Than Other Sugars?". Archives of Biochemistry and Biophysics vol. 360, No. 1, Dec. 1, pp. 10-14, 1998 (Year: 1998).*

Alfaro et al., "Trehalose-mediated thermal stabilization of glucose oxidase from Aspergillus niger", Journal Of Biotechnology, Elsevier, Amsterdam, NL, vol. 141, No. 3-4, May 20, 2009, pp. 130-136.

Gavalas et al., "Polyelectrolyte stabilized oxidase based biosensors: effect of diethylaminoethyl-dextran on the stabilization of glucose and lactate oxidases into porous conductive carbon", Analytica chimica acta, vol. 404, No. 1, Jan. 1, 2000, pp. 67-73.

International Preliminary Report on Patentability received for PCT Patent Application No. PCT/US2020/034279, mailed on Dec. 9, 2021, 11 pages.

International Search Report and Written Opinion received for PCT Patent Application No. PCT/US2020/034279, mailed on Aug. 11, 2020, 19 pages.

Ye et al., "Influence of additives on the thermostability of glucose oxidase", Enzyme And Microbial Technology, vol. 10, No. 8, Aug. 1, 1988, pp. 498-502.

* cited by examiner

STABILIZED MEDICAL DEVICES AND ASSOCIATED METHODS

CROSS REFERENCE TO RELATED APPLICATION

This application is a national phase application of PCT Application No. PCT/US2020/034279, internationally filed on May 22, 2020, which claims the benefit of Provisional Application No. 62/853,499, filed May 28, 2019, which are incorporated herein by reference in their entireties for all purposes.

FIELD

The present disclosure relates generally to stabilized medical devices including substrate materials having immobilized biologically active entities necessary for sterilization, and more specifically to stabilized analyte sensors and stabilized biobatteries and associated methods thereof.

BACKGROUND

Before medical devices such as stents, catheters, and sensors can be inserted into a patient's body, the devices must be sterilized to ensure no contaminants are present. Contaminants such as bacteria, viruses, and other various impurities can harm the patient. For example, impurities present on medical devices can result in the emergence or spread of infections and diseases, allergic reactions, and poisoning. Sterilization of such devices generally requires exposure of the devices to elevated temperatures, pressure, and humidity with sterilization often requiring several cycles.

Common methods for sterilizing medical devices may include gaseous agents such as ethylene oxide (ETO) or vapor hydrogen peroxide (VHP), for example. Other sterilization methods include gamma radiation sterilization, and the like. ETO and VHP sterilization are effective at killing micro-organisms at temperatures lower than those required for heat sterilization techniques. Thus, ETO and VHP sterilization can be used for medical devices containing materials incapable of withstanding high temperatures, such as analyte sensors that utilize various biological components. ETO and VHP sterilization can also be used for medical devices having complex geometries, because ETO and VHP gas are capable of surrounding and infiltrating the device. However, one disadvantage of ETO and VHP sterilization is its damaging effect (e.g., degradation, denaturing, undesired chemical reaction, decomposition, etc.) on biological components that are necessary for operation of the device. Examples of biological components can include, for example, enzymes, antibodies, aptamers, and ligands configured to sense analytes or other constituents in the patient's body. Thus, there is a need for devices with stabilized biological components for medical devices having biologically active entities immobilized thereon that do not degrade during sterilization and/or storage and retain a suitable level of biological activity after implantation in the patient's body.

SUMMARY

According to one example ("Example 1"), a stabilized medical device includes a substrate that is at least partially electrically conductive and a stabilized enzyme layer disposed over at least a portion of a surface of the substrate, the stabilized enzyme layer including at least one biologically active sensing component, and at least one stabilizing component non-covalently combined with the biologically active sensing component, the biologically active sensing component having a biological activity detection level from about 25 U/cm3 to about 1,000,000 U/cm3 of the substrate following ethylene oxide sterilization of the biologically active sensing component.

According to another example ("Example 2") further to Example 1, the biologically active sensing component is selected from the group consisting of: trehalose, diethylaminoethyl-dextran hydrochloride, and sorbose.

According to another example ("Example 3") further to Examples 1 or 2, the biologically active sensing component has a biological activity detection level after ethylene oxide sterilization that is within from about 45% to about 95% of a biological activity detection level before ethylene oxide sterilization.

According to another example ("Example 4") further to any one of preceding Examples 1 to 3, the biologically active sensing component has a biological activity detection level after ethylene oxide sterilization that is within from about 50% to about 90% of a biological activity detection level before ethylene oxide sterilization.

According to another example ("Example 5") further to any one of preceding Examples 1 to 4, a mass ratio of the stabilizing component to the biologically active sensing component in the stabilized enzyme layer is from about 0.1 to about 10,000.

According to another example ("Example 6") further to any one of preceding Examples 1 to 5, a mass ratio of the stabilizing component to the biologically active sensing component in the stabilized enzyme layer is from about 10 to about 50.

According to another example ("Example 7") further to any one of preceding Examples 1 to 6, the biologically active sensing component has a biological activity detection level from about 25 U/cm3 to about 1,000,000 U/cm3 of the substrate following ethylene oxide sterilization of the biologically active sensing component.

According to another example ("Example 8") further to any one of preceding Examples 1 to 7, the substrate comprises electrically conductive ePTFE.

According to another example ("Example 9") further to any one of preceding Examples 1 to 8, the biologically active sensing component is configured to sense a level of glucose oxidase in a body of a patient.

According to one example ("Example 10"), a method for making a stabilized medical device includes mixing at least one stabilizing component with at least one sensing component to form a stabilized mixture, coating an electrically conductive substrate with the stabilized mixture to form a stabilized enzyme layer on at least a portion of the substrate, and subjecting the substrate to an ethylene oxide sterilization process, the sensing component having a biological activity detection level after sterilization that is within from about 45% to about 95% of the biological activity detection level before sterilization.

According to another example ("Example 11") further to Example 10, the sensing component is selected from the group consisting of: trehalose, diethylaminoethyl-dextran, and sorbose.

According to another example ("Example 12") further to any one of preceding Examples 10 to 11, the sensing component has a biological activity detection level after sterilization that is within about 40% to about 90% of the biological activity detection level before sterilization.

According to another example ("Example 13") further to any one of preceding Examples 10 to 12, the stabilizing component and the sensing component are mixed at a mass ratio of about 0.1 to about 10,000.

According to another example ("Example 14") further to any one of preceding Examples 10 to 13, the stabilizing component and the sensing component are mixed at a mass ratio of about 10 to about 50.

According to another example ("Example 15") further to any one of preceding Examples 10 to 14, the sensing component has a biological activity detection level from about 25 U/cm3 to about 1,000,000 U/cm3 of the substrate following ethylene oxide sterilization of the biologically active sensing component.

According to another example ("Example 16") further to any one of preceding Examples 10 to 15, the sensing component has biological activity detection level from about 25 U/cm3 to about 1,000,000 U/cm3 of the substrate following ethylene oxide sterilization of the biologically active sensing component.

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

The present disclosure relates generally to stabilized medical devices such as stabilized, implantable analyte sensors and biobatteries that are both biocompatible and stable over a long period of time. More particularly, the present disclosure relates to analyte sensors and biobatteries including biological components that have been non-covalently stabilized to withstand sterilization processes, such as ETO or VHP sterilization. The stabilized analyte sensors and sensor materials disclosed herein can have improved performance and accuracy of sensor readings as compared to analyte sensors and sensor materials that have not been stabilized prior to undergoing sterilization processes.

This disclosure is not meant to be read in a restrictive manner. For example, the terminology used in the application should be read broadly in the context of the meaning those in the field would attribute such terminology. The term "stabilized" as used herein is meant to denote that the biological component is capable of being sterilized while maintaining adequate biological activity for its intended function or use.

Figure 1:
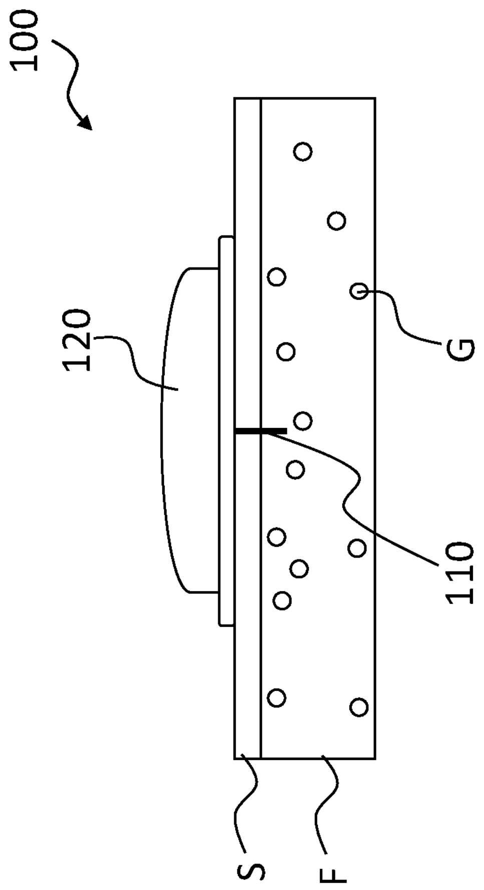
FIG. 1 is a schematic view of a stabilized medical device including a processor and an analyte sensor implanted into a patient's skin, in accordance with an embodiment.

FIG. 1 is a schematic view of a stabilized medical device 100 including a processor 120 and a stabilized analyte sensor 110 implanted into a patient's skin S, in accordance with an embodiment. As shown, the device 100 includes the processor 120 resting on the surface of the patient's skin S and the stabilized analyte sensor 110 implanted through the patient's skin S and contacting the patient's interstitial fluid F. The device 100 is configured to detect a desired analyte (e.g., glucose G, oxygen, hydrogen peroxide, biomarker, protein, etc.) in the patient's interstitial fluid F. In some instances, the stabilized analyte sensor 110 may transmit a signal to the processor 120, and the processor 120 may then process the signal into a suitable output (e.g., an analyte concentration) to be read by the patient or the patient's practitioner. Though the device 100 is described in the present disclosure in reference to detecting glucose (e.g., a glucose sensor), the present disclosure is also applicable to other types of sensor systems used in other locations and/or to detect other types of analytes.

Figure 2:
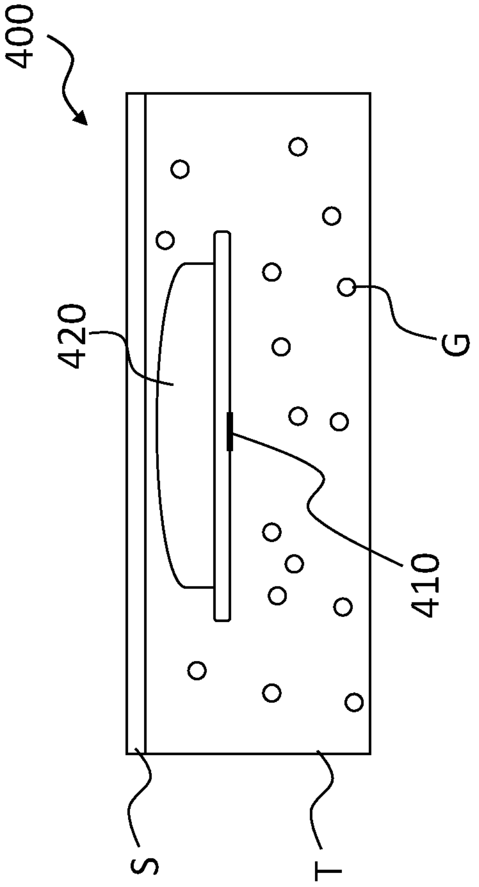
FIG. 2 is a schematic view of a stabilized medical device including a processor and an analyte sensor implanted into a patient, in accordance with an embodiment.

FIG. 2 is a schematic view of a stabilized medical device 400 including a processor 420 (similar to processor 120) and a stabilized analyte sensor 410 (similar to sensor 110) fully implanted into a patient's tissue T, in accordance with an embodiment. As shown, the device 400 includes the processor 420 resting under the surface of the patient's skin S and the stabilized analyte sensor 410 implanted within the patient's tissue T and exposed to interstitial fluid. Tissue T may be connective, subcutaneous, or organ tissue and is beneath outermost layer of skin S. The device 400 is configured to detect a desired analyte (e.g., glucose G, oxygen, hydrogen peroxide, biomarker, protein, etc.) in the patient's tissue T. In some instances, the stabilized analyte sensor 410 may transmit a signal to the processor 420, and the processor 420 may then process the signal into a suitable output (e.g., an analyte concentration) to be read by the patient or the patient's practitioner. Though the device 400 is described in the present disclosure in reference to detecting glucose (e.g., a glucose sensor), the present disclosure is also applicable to other types of sensor systems used in other locations and/or to detect other types of analytes.

Figure 3:
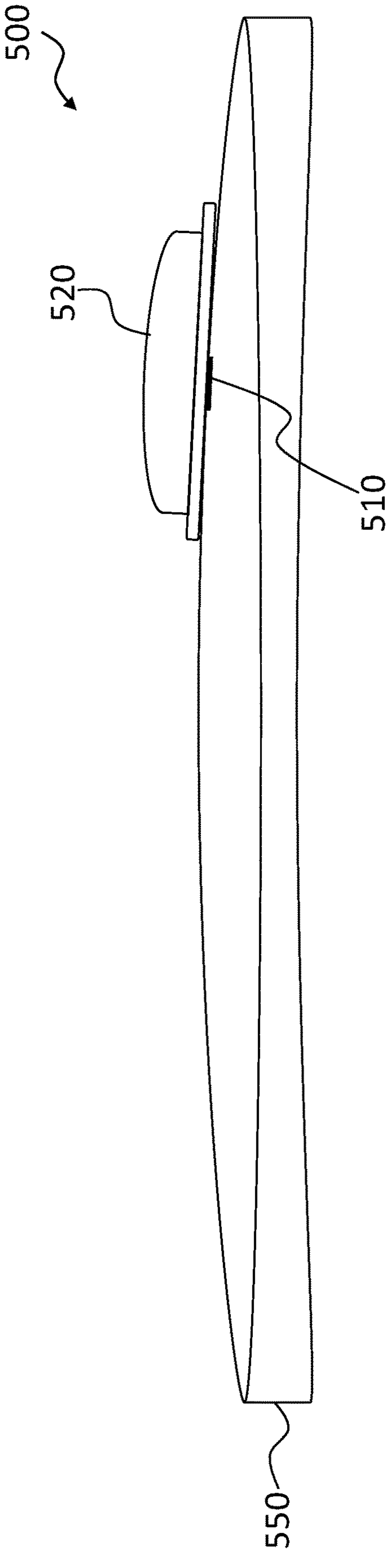
FIG. 3 is a schematic view of a stabilized medical device including a processor and an analyte sensor in contact with a patient but not implanted, in accordance with an embodiment.

FIG. 3 is a schematic view of a stabilized medical device 500 including a processor 520 (similar to processor 120) and a stabilized analyte sensor 510 (similar to sensor 110) for placement in contact with a patient but without implantation, in accordance with an embodiment. As shown, the device 500 includes the processor 520 and the stabilized analyte sensor 510 for a patient, e.g. the device 500 for use on a contact lens 550. The device 500 is configured to detect a desired analyte (e.g., glucose, oxygen, hydrogen peroxide, biomarker, protein, etc.) on the patient, for example detected from the moisture associated with the patient's eye. In some instances, the stabilized analyte sensor 510 may transmit a signal to the processor 520, and the processor 520 may then process the signal into a suitable output (e.g., an analyte concentration) to be read by the patient or the patient's practitioner. Though the device 500 is described in the present disclosure in reference to detecting glucose (e.g., a glucose sensor), the present disclosure is also applicable to other types of sensor systems used in other locations and/or to detect other types of analytes. For example, sweat from skin can be utilized to detect cortisol or fluid from a wound can be utilized to detect a desired analyte.

Figure 4:
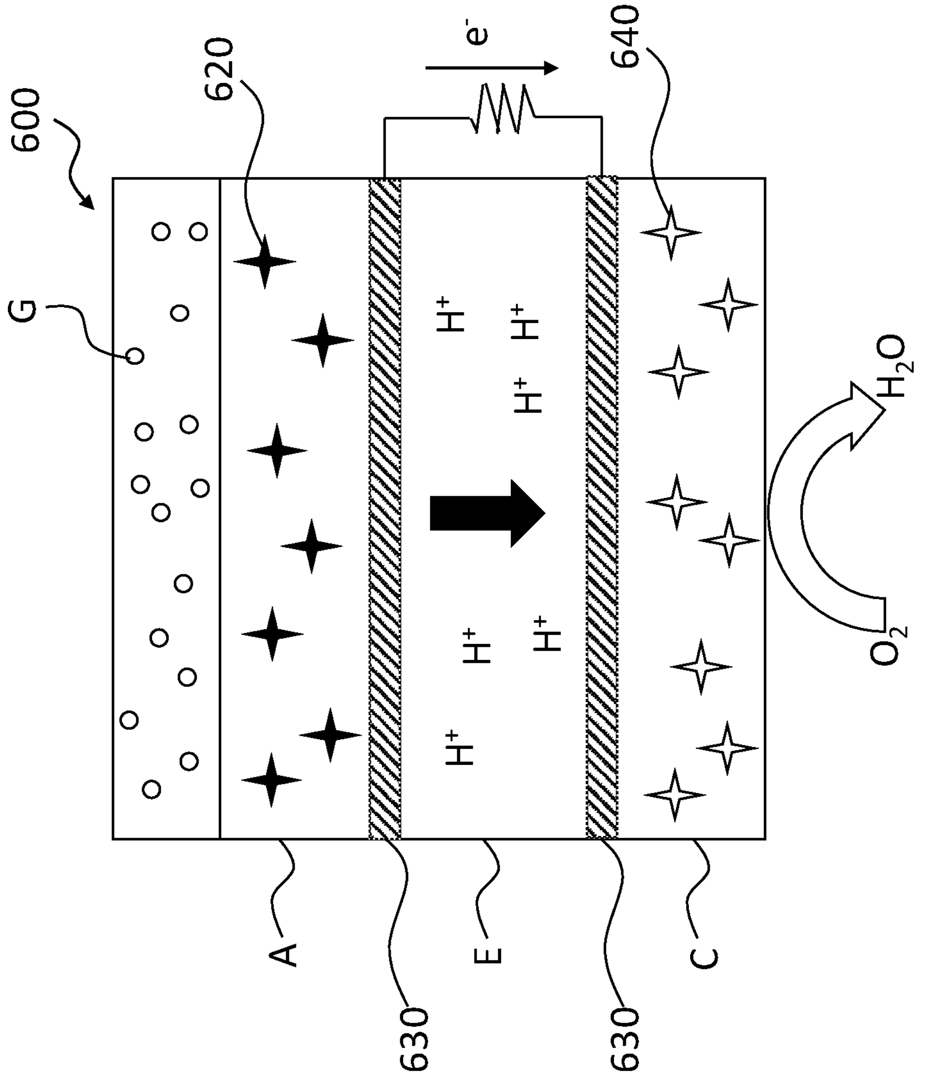
FIG. 4 is a schematic view of a biobattery, in accordance with an embodiment.

FIG. 4 is a schematic view of a biobattery 600, in accordance with an embodiment. A biobattery is an energy conversion and storage device that is powered by organic compounds such as carbohydrates, e.g. glucose in human blood. As enzymes in human bodies break down glucose, electrons and protons are released thereby providing energy to the biobattery, which may be stored for later use. Biobattery 600 includes an anode A, a cathode C, and an electrolyte E separated from the anode A and the cathode C by semi-permeable membranes 630. Anode A is in contact with an organic compound such as glucose G. Biological components such as glucose-digesting enzymes 620 are immobilized on anode A and oxygen-reducing compounds or enzymes 640 are immobilized on the cathode C. Electrons $e^-$ are released as energy. Cathode C is exposed to an environment rich in oxygen $O_2$ so that the $H^+$ ions combine with the $O_2$ to produce water $H_2O$. Applications for biobattery medical devices may include artificial pacemakers, external hearing devices, battery-operated insulin pumps, digital thermometers, and glucose meters used by diabetics. In an alternative embodiment, a battery that provides the primary power for such devices can be recharged by the biobattery to extend useful lifespan of devices without intervention to replace the primary battery. Biobattery 600 may be implanted in a patient. Alternatively, the biobattery may be placed on the skin of a patient in a manner whereby the organic power source (e.g., glucose) is accessible by the biobattery.

Figure 5:
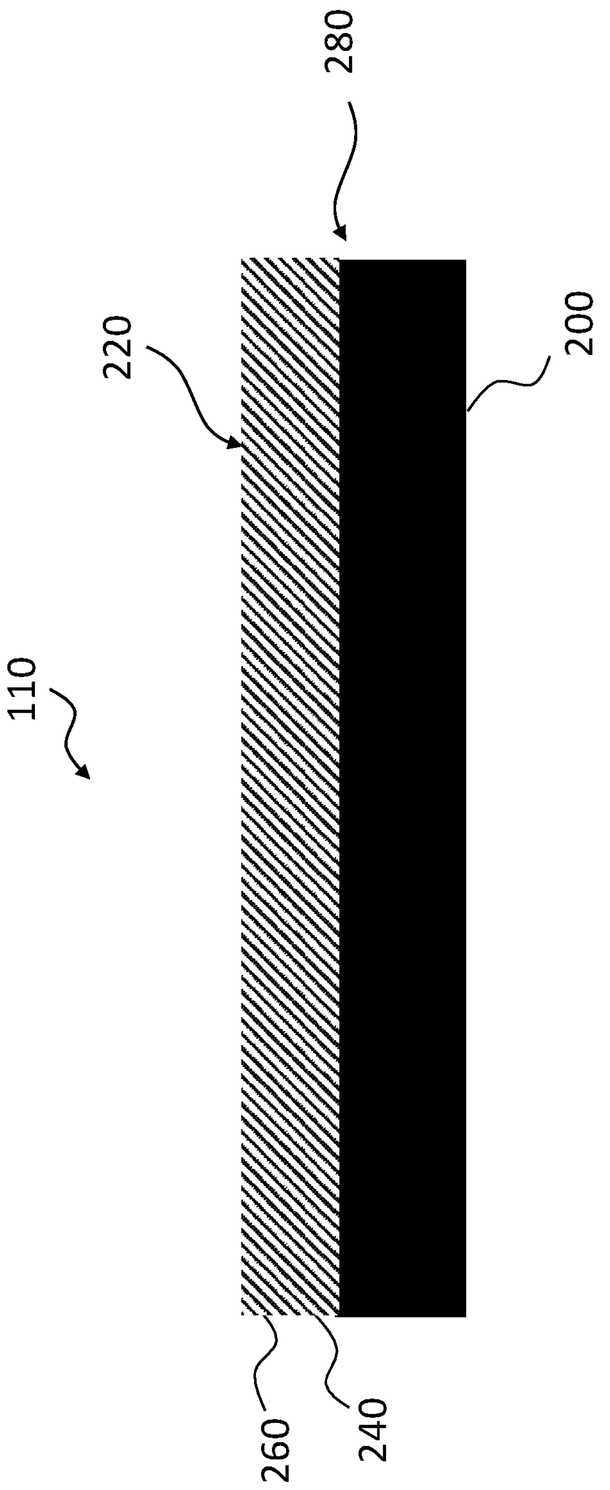
FIG. 5 is a schematic view of a surface of the analyte sensor of FIG. 1, in accordance with an embodiment.

FIG. 5 is a schematic view of a surface of the stabilized analyte sensor 110 of FIG. 1. As shown, the stabilized analyte sensor 110 includes a substrate 200 and a stabilized enzyme layer 220 disposed over at least a portion of the surface of the substrate 200. These teachings may also be applied to the sensor 410 of FIG. 2, the sensor 510 of FIG. 3, and the anode A, cathode C, and/or other elements of the biobattery 600 of FIG. 4.

The substrate 200 is at least partially electrically conductive. For example, the substrate 200 may include expanded polytetrafluoroethylene (ePTFE) that has been rendered electrically conductive by coating with a conductive metal, extruding with a conductive material, or any other suitable techniques as will be known to those skilled in the art.

Figure 6:
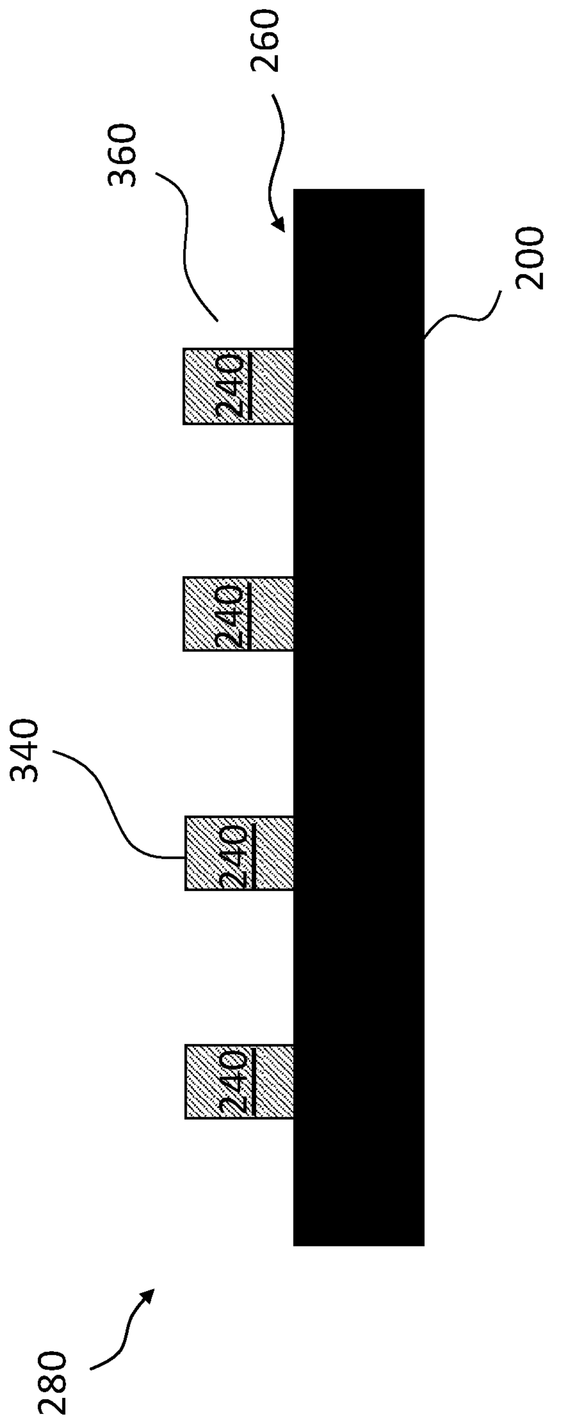
FIG. 6 is a close-up schematic view of an interface between a stabilizing component and a sensing component of the analyte sensor of FIG. 5, in accordance with an embodiment.

Referring to FIG. 5 and FIG. 6, the stabilized enzyme layer 220 includes a sensing component 240. As used herein, the phrase "sensing component" means a sensitive biological component capable of interacting with or recognizing the desired analyte to be detected. For example, the sensing component 240 may include enzymes capable of reacting with the analyte being detected. In the case of glucose sensors, the enzyme may include, for example, glucose oxidase, which is capable of reacting with glucose G (e.g., the analyte) in the patient's interstitial fluid F (FIG. 1) to convert the glucose G into a product that is detectable by the sensor 120 (e.g., hydrogen peroxide or other constituents).

In some instances, the stabilized enzyme layer 220 including the sensing component 240 is attached to at least a portion of the surface of the substrate 200. For example, the sensing component 240 may bond with the surface of the substrate 200 when in contact with the substrate 200.

The stabilized enzyme layer 220 also includes a stabilizing component 260 combined with the sensing component 240. In some instances, the stabilizing component 260 includes at least one of trehalose, diethylaminoethyl-dextran hydrochloride, and/or sorbose. In some instances, the stabilizing component 260 is non-covalently combined with the sensing component 240. For example, the stabilizing component 260 and the sensing component 240 may be physically mixed with one another during formation of the stabilized enzyme layer 220 without being covalently bonded to one another.

FIG. 6 is a close-up schematic view of an interface 280 between the stabilizing component 260 and the sensing component 240 of the analyte sensor 110 (FIG. 5). As shown, molecules 360 of the stabilizing component 260 are combined (e.g., admixed) with molecules 340 of the sensing component 240 without being covalently bonded to one another.

In some instances, the stabilizing component 260 may be non-covalently combined with the sensing component 240 at a mass ratio from about 0.1 to about 10,000 of the stabilizing component 260 to the sensing component 240 in the stabilized enzyme layer 220, or from 10 to about 100 of the stabilizing component 260 to the sensing component 240 in the stabilized enzyme layer 220, or from about 10 to about 50 of the stabilizing component 260 to the sensing component 240 in the stabilized enzyme layer 220. Combining at such ratios stabilizes the sensing component 240 and ensures that the biological activity of the sensing component 240 is preserved.

In some instances, the biological activity of the sensing component 240 can be characterized by a biological activity detection level of the sensing component 240. As used herein, the phrase "biological activity detection level" generally means the ability of the sensing component 240 to detect a given number of analytes in a sample. In some instances, the biological activity detection level of a non-stabilized sensing component after ETO sterilization is less than about 20%, less than about 10%, or less than about 5% of the biological activity detection level of the non-stabilized sensing component before ETO sterilization, whereas the biological activity detection level of the stabilized sensing component 240 after ETO sterilization is from about 45% to about 95% of the biological activity detection level before ETO sterilization, within from about 50% to about 90% of the biological activity detection level before ETO sterilization, or within from about 50% to about 80% of the biological activity detection level before ETO sterilization.

In some instances, the biological activity of the biobattery 600 can be characterized by a biological activity level of recharging a primary battery of a device. As used herein, the phrase "biological activity recharging current level" generally means the ability of the anode and cathode to generate a minimum current.

In some instances, the sensing component 240 may have a biological activity detection level from about 25 U/cm$^3$ to about 1,000,000 U/cm$^3$ of substrate 200 following ETO sterilization of the stabilized analyte sensor 110, or from about 100 U/cm$^3$ to about 300 U/cm$^3$ of substrate 200 following ETO sterilization of the stabilized analyte sensor 110.

Figure 7:
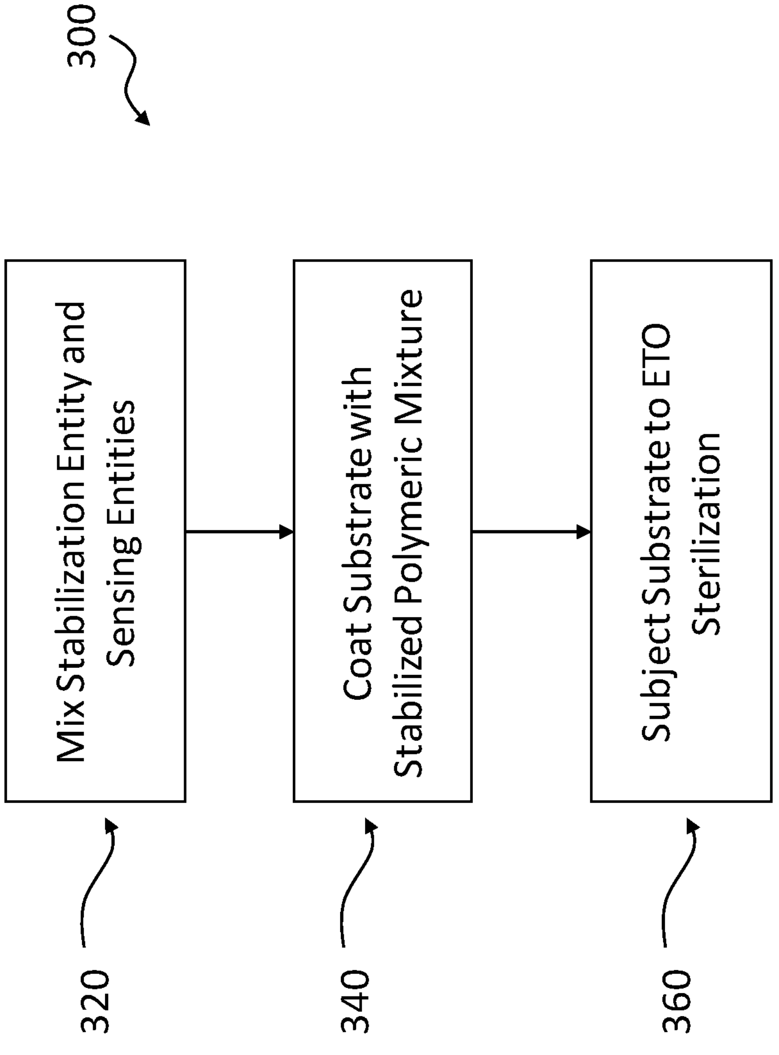
FIG. 7 is a flow diagram showing a method of making a stabilized medical device, in accordance with an embodiment.

FIG. 7 is a flow diagram showing a method 300 of making the stabilized medical device described herein, in accordance with an embodiment. The method 300 is described with reference to the components described above and shown in FIGS. 1 through 5. The method 300 includes non-covalently combining (e.g., admixing) the stabilizing component 260 with the sensing component 240 to form a stabilized polymeric mixture, in a mixing step 320. The mixture is then coated onto the substrate 200 to form the stabilized enzyme layer 220 thereon, in a coating step 340. For example, in some instances, the substrate 200 may be dip coated in the mixture so that a generally thin and even layer is formed thereon. After dip coating, the substrate 200 may be dried by exposure to ambient condition or by forced air drying. After coating, the substrate 200 and stabilized enzyme layer 220 are subjected to an ETO sterilization process, in sterilizing step 360.

EXAMPLES

It should be understood that although certain methods and equipment are described below, other methods or equipment determined suitable by one of ordinary skill in the art may be alternatively utilized.

Comparative Example 1: Effect of Zinc Sulfate on Glucose Oxidase Activity Before and After Ethylene Oxide Sterilization A stabilized mixture was prepared by mixing unsterilized glucose oxidase with zinc sulfate. The unsterilized glucose oxidase (*Aspergillus Niger*, G7141) in lyophilized powder form was obtained from Sigma-Aldrich (St. Louis, MO). A working solution of glucose oxidase at 1 mg/mL was prepared in deionized (DI) water. Zinc sulfate in unsterilized powder form was obtained from Sigma-Aldrich (St. Louis, MO). Working solutions at 0.001 mg/mL, 0.01 mg/mL, 0.1 mg/mL, 1.0 mg/mL, 10.0 mg/mL, and 100.0 m g/m L were prepared in DI water.

1-mL aliquots of the working glucose oxidase solution were added to 2-mL glass vials along with 1-mL of the working zinc sulfate solution for each of the prepared concentrations. This yielded, on a mass per mass basis, mass ratios of 0.001, 0.01, 0.1, 1.0, 10.0, and 100.0 of zinc sulfate to glucose oxidase, respectively. Four vials of control samples were prepared that contained 1 mL each of the working glucose oxidase solution with no working zinc sulfate solution.

Each of the vials was capped, placed on a shaker tray to ensure mixing of the solution, frozen, and lyophilized over a period of several days to produce a powder in the vial. ETO sterilization was then carried out for a group of the samples for about 1-hr (e.g., at an ETO gas dwell time of 1-hr) at a temperature of approximately 55 degrees C. and an average aeration time of 12 hours. A second group of samples was not subjected to ETO sterilization and maintained at room temperature. A third group of samples was not subjected to ETO sterilization and was frozen at −15 degrees C.

Following the sterilization procedure, each of the groups of samples were examined for biological activity. A glucose oxidase activity analysis was carried out using a Utilized Amplex™ Red Glucose/Glucose Oxidase Assay Kit (ThermoFisher, A22189). For dilutions, a modified buffer solution was then prepared that consisted of 25 mM phosphate buffer (pH 7.4), 100 μg/mL bovine serum albumin, 5.7 g/L $KH_2PO_4$, and 54.325 g/L $Na_2HPO_4.7H_2O$. The fluorescence was then measured at 530 nm excitation and 590 nm emission in kinetic mode, measuring every 1 minute for at least 5 minutes.

Figure 8:
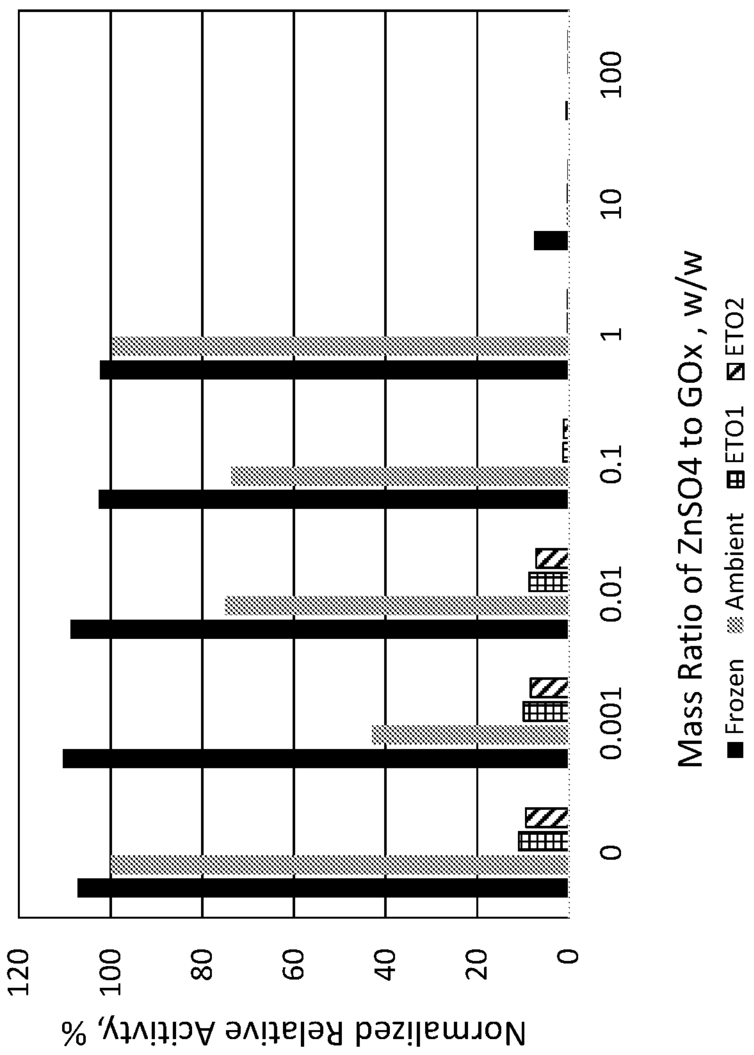
FIG. 8 is a graph showing the effect of zinc sulfate on glucose oxidase activity before and after ETO sterilization, in accordance with an embodiment.

FIG. 8 is a graph showing the effect of zinc sulfate ($ZnSO_4$) on glucose oxidase (GOx) activity before and after ETO sterilization. The activity of glucose oxidase was expressed as normalized relative activity by dividing the measured activity for each sample by the measured value of a pure glucose oxidase control sample at room temperature and multiplying by 100 to yield a percentage. The pure glucose oxidase was obtained from the manufacturer's container and was not sterilized.

As shown in FIG. 8, sterilized glucose oxidase samples that received no zinc sulfate showed a reduction in normalized relative activity compared to the control samples (e.g., samples that were not sterilized and were maintained at room temperature or frozen). The normalized relative activity of the room temperature control samples was 100%. The normalized relative activity of the frozen samples was 107%. However, the normalized relative activities of the sterilized samples were approximately 10.8% and 9.4%, respectively. As shown in FIG. 8, ETO1 and ETO2 denote duplicate samples for the ETO sterilization. Thus, it was concluded that ETO sterilization caused an approximate 90% reduction in biological activity of the glucose oxidase as compared to unsterilized samples. It was also concluded that the addition of zinc sulfate to the glucose oxidase did not substantially increase the biological activity of the glucose oxidase after ETO sterilization. At the highest mass ratio of zinc sulfate to glucose oxidase of 100, the normalized relative activity was below 0.2% demonstrating an inability to maintain activity. For the samples that were not sterilized, zinc sulfate demonstrated deactivation of activity. For frozen samples at the 10 and 100 mass ratios of zinc sulfate to glucose oxidase, activity levels fell to less than 10%. Those maintained at room temperature showed activity levels far below 5%. These results demonstrate the inability to maintain, or increase, the glucose oxidase activity following EtO sterilization with zinc sulfate combined with glucose oxidase.

Example 2: Effect of Trehalose on Glucose Oxidase Activity Before and After Ethylene Oxide Sterilization A stabilized mixture was prepared by mixing unsterilized glucose oxidase with trehalose. The unsterilized glucose oxidase (*Aspergillus Niger*, G7141) in lyophilized powder form was obtained from Sigma-Aldrich (St. Louis, MO). A working solution of trehalose at 1 mg/mL was prepared in deionized (DI) water. Trehalose in unsterilized powder form was obtained from Sigma-Aldrich (St. Louis, MO). Working solutions at 0.001 mg/mL, 0.01 mg/mL, 0.1 mg/mL, 1.0 mg/mL, 10.0 mg/mL, and 100.0 mg/mL were prepared in DI water.

1-mL aliquots of the working glucose oxidase solution were added to 2-mL glass vials along with 1-mL of the working trehalose solution for each of the prepared concentrations. This yielded, on a mass per mass basis, mass ratios of 0.001, 0.01, 0.1, 1.0, 10.0, and 100.0 of trehalose to glucose oxidase, respectively. Four vials of control samples were prepared that contained 1 mL each of the working glucose oxidase solution with no working trehalose solution.

Each of the vials was capped, placed on a shaker trap to ensure mixing of the solution, frozen, and lyophilized over a period of several days to produce a powder in the vial. ETO sterilization was then carried out for a group of samples for about 1-hr (e.g., at an ETO gas dwell time of 1-hr) at a temperature of approximately 55 degrees C. and an average aeration time of 12 hours. A second group of samples was not subjected to ETO sterilization and maintained at room temperature. A third group of samples was not subjected to ETO sterilization and was frozen at −15 degrees C.

Following the sterilization procedure, each of the groups of samples were examined for biological activity as described in Example 1.

Figure 9:
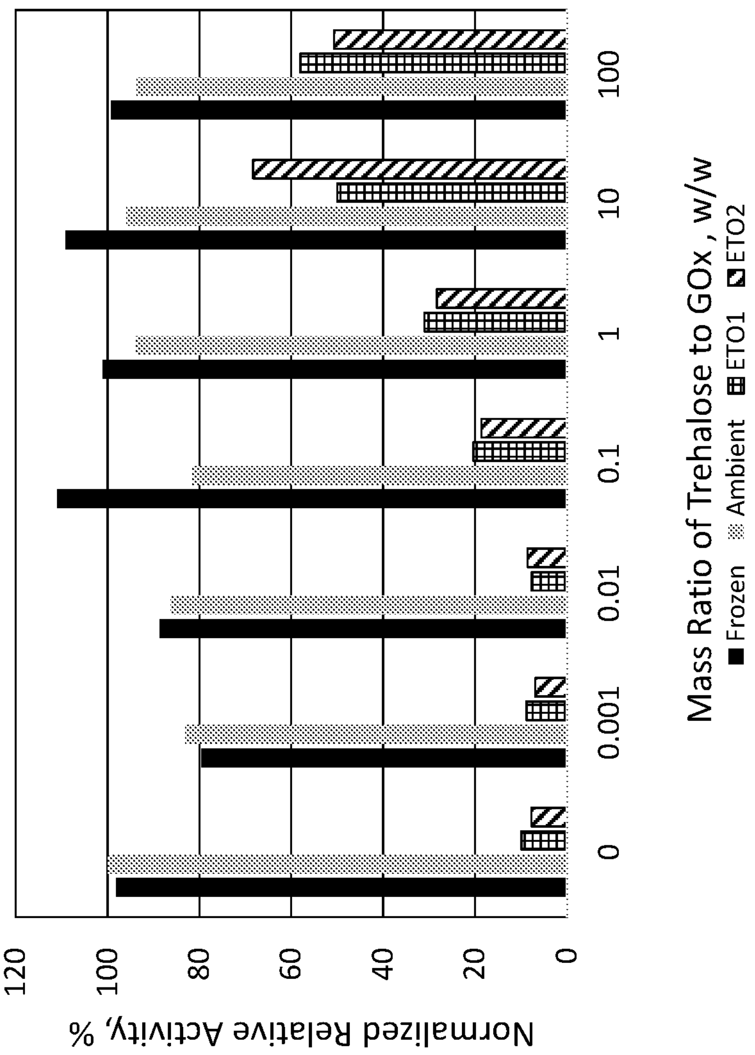
FIG. 9 is a graph showing the effect of trehalose on glucose oxidase activity before and after ETO sterilization, in accordance with an embodiment.

FIG. 9 is a graph showing the effect of trehalose on glucose oxidase activity before and after ETO sterilization. The activity of glucose oxidase was expressed as normalized relative activity by dividing the measured activity for each sample by the measured value of a pure glucose oxidase control sample at room temperature and multiplying by 100 to yield a percentage. The pure glucose oxidase was obtained from the manufacturer's container and was not sterilized.

As shown in FIG. 9, sterilized glucose oxidase samples that received no trehalose showed a fairly large reduction in normalized relative activity compared to the control samples (e.g., samples that were not sterilized and were maintained at room temperature or frozen). The normalized relative activity of the room temperature control samples was 100%. The normalized relative activity of the frozen samples was 89%. The normalized relative activity of the sterilized samples that did not include trehalose was approximately 9.8% and 7.7%, respectively. Thus, it was concluded that ETO sterilization caused an approximate 90% reduction in biological activity of the glucose oxidase as compared to unsterilized samples. The normalized relative activity of unsterilized samples treated with trehalose, and maintained at room temperature, varied from 82% to 96% and those maintained frozen at −15 C varied from 79% to 111%. A reduction in normalized relative activity level was shown by the room temperature samples at the mass of trehalose to GOx of 0.001, 0.01., and 0.1 as the activity ranged from 82% to 86%. Higher mass ratios of trehalose demonstrated substantially no effect on activity for this group. The frozen samples showed activity reduction for mass of trehalose to GOx for 0.001 and 0.01.

The sterilized samples having a mass ratio of 0.001 and 0.01 of trehalose to glucose oxidase showed little increase in biological activity as compared to the sterilized samples that did not include trehalose. The sterilized samples having a mass ratio of 0.1, 1, 10, and 100 of trehalose to glucose oxidase showed an increase in biological activity as compared to the sterilized samples that did not include trehalose. As shown, the biological activity of sterilized samples having a mass ratio of 0.1 and 1 ranged from about 18% to 20% and from about 28% to 31%, respectively. As shown, the biological activity of sterilized samples having a mass ratio of 10 and 100 ranged from about 50% to 68% and from about 51% to 58%, respectively. Thus, it was concluded that trehalose at mass ratios of about 10 to 100 of trehalose to glucose oxidase increases biological activity of the glucose oxidase after ETO sterilization as compared to samples having no trehalose. Further, these results demonstrated the ability to maintain the glucose activity of GOx following EtO sterilization with an appropriate biologically compatible composition non-covalently combined with GOx in powder form.

Example 3: Effect of Sorbose on Glucose Oxidase Activity Before and After Ethylene Oxide Sterilization A stabilized mixture was prepared by mixing unsterilized glucose oxidase with sorbose. The unsterilized glucose oxidase (*Aspergillus Niger*, G7141) in lyophilized powder form was obtained from Sigma-Aldrich (St. Louis, MO). A working solution of glucose oxidase at 1 mg/mL was prepared in deionized (DI) water. Sorbose in unsterilized powder form was obtained from Sigma-Aldrich (St. Louis, MO). Working solutions at 0.001 mg/m L, 0.01 mg/mL, 0.1 mg/mL, 1.0 mg/mL, 10.0 mg/mL, and 100.0 mg/mL were prepared in DI water.

1-mL aliquots of the working glucose oxidase solution were added to 2-mL glass vials along with 1-mL of the working sorbose solution for each of the prepared concentrations. This yielded, on a mass per mass basis, mass ratios of 0.001, 0.01, 0.1, 1.0, 10.0, and 100.0 of sorbose to glucose oxidase, respectively. Four vials of control samples were prepared that contained 1 mL each of the working glucose oxidase solution with no working sorbose solution.

Each of the vials was capped, placed on a shaker trap to ensure mixing of the solution, frozen, and lyophilized over a period of several days to produce a powder in the vial. ETO sterilization was then carried out for a group of samples for about 1-hr (e.g., at an ETO gas dwell time of 1-hr) at a temperature of approximately 55 degrees C. and an average aeration time of 12 hours. A second group of samples was not subjected to ETO sterilization and maintained at room temperature. A third group of samples was not subjected to ETO sterilization and was frozen at −15 degrees C.

Following the sterilization procedure, each of the groups of samples were examined for biological activity as described in Example 1.

Figure 10:
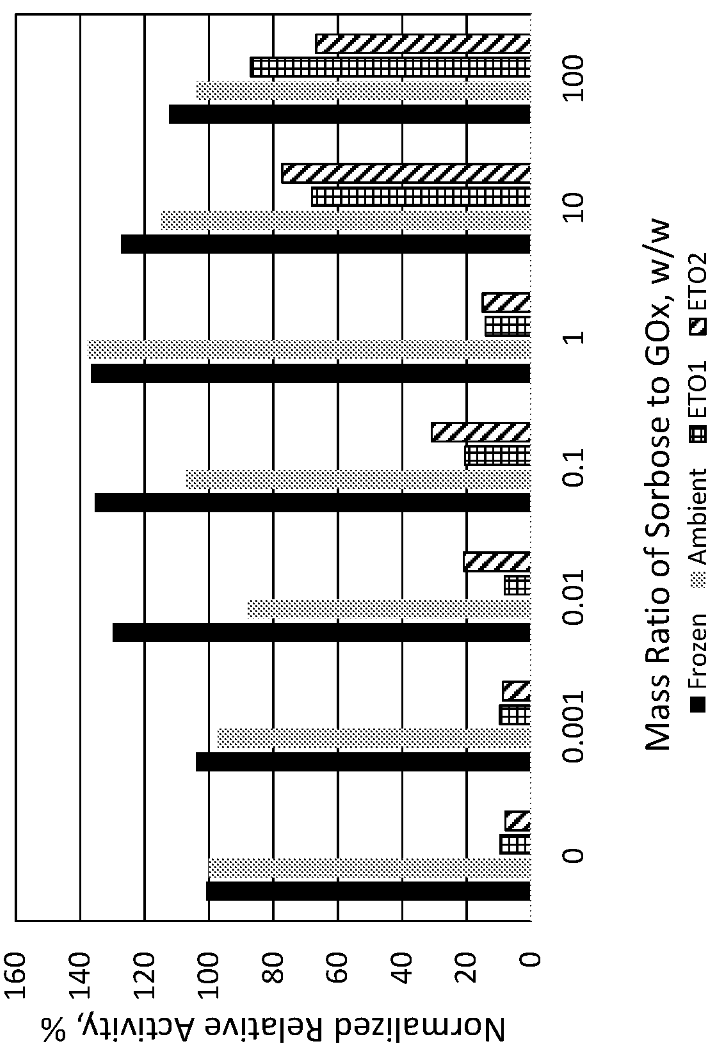
FIG. 10 is a graph showing the effect of sorbose on glucose oxidase activity before and after ETO sterilization, in accordance with an embodiment.

FIG. 10 is a graph showing the effect of sorbose on glucose oxidase activity before and after ETO sterilization. The activity of glucose oxidase was expressed as normalized relative activity by dividing the measured activity for each sample by the measured value of a pure glucose oxidase control sample at room temperature and multiplying by 100 to yield a percentage. The pure glucose oxidase was obtained from the manufacturer's container and was not sterilized.

As shown in FIG. 10, sterilized glucose oxidase samples that received no sorbose showed a fairly large reduction in normalized relative activity compared to the control samples (e.g., samples that were not sterilized and were maintained at room temperature or frozen). The normalized relative activity of the room temperature control samples was 100%. The normalized relative activity of the frozen samples was 101%. The normalized relative activity of the sterilized samples that did not include sorbose was approximately 9.4% and 7.9%, respectively. Thus, it was concluded that ETO sterilization caused an approximate 90% reduction in biological activity of the glucose oxidase as compared to unsterilized samples.

The normalized relative activity of unsterilized samples treated with sorbose, and maintained frozen at −15 C, showed an enhancement effect at a mass ratio of 0.01, 0.1, 1, and 10 as the normalized relative activity values were all above 120%. This effect was somewhat diminished at a mass ratio of 100 with an activity value of 112%. The room temperature samples showed an enhancement effect at a mass ratio of 1 and 10 with activity values of 135% and 115% respectively.

The sterilized samples having a mass ratio of 0.0001 and 0.01 of sorbose to glucose oxidase showed little increase in biological activity as compared to the sterilized samples that did not include sorbose. The sterilized samples having a mass ratio of 0.1, 1, 10, and 100 of sorbose to glucose oxidase showed an increase in biological activity as compared to the sterilized samples that did not include sorbose. As shown, the biological activity of sterilized samples having a mass ratio of 0.1 and 1 ranged from about 20% to 31% and from about 14% to 15%, respectively. As shown, the biological activity of sterilized samples having a mass ratio of 10 and 100 ranged from about 68% to 77% and from about 67% to 87%, respectively. Thus, it was concluded that sorbose at mass ratios of about 10 to 100 of sorbose to glucose oxidase increases biological activity of the glucose oxidase after ETO sterilization as compared to samples having no sorbose. Further, these results demonstrated the ability to maintain the glucose activity of GOx following EtO sterilization with an appropriate biologically compatible composition non-covalently combined with GOx in powder form.

Example 4: Effect of Diethylaminoethyl-Dextran on Glucose Oxidase Activity Before and After Ethylene Oxide Sterilization A stabilized mixture was prepared by mixing unsterilized glucose oxidase with diethylaminoethyl-dextran (DEAE-dextran). The unsterilized glucose oxidase (*Aspergillus Niger*, G7141) in lyophilized powder form was obtained from Sigma-Aldrich (St. Louis, MO). A working solution of glucose oxidase at 1 mg/mL was prepared in deionized (DI) water. DEAE-dextran in unsterilized powder form was obtained from Sigma-Aldrich (St. Louis, MO). Working solutions at 0.001 mg/mL, 0.01 mg/mL, 0.1 mg/mL, 1.0 mg/mL, 10.0 mg/mL, and 100.0 mg/mL were prepared in DI water.

1-mL aliquots of the working glucose oxidase solution were added to 2-mL glass vials along with 1-mL of the working DEAE-dextran solution for each of the prepared concentrations. This yielded, on a mass per mass basis, mass ratios of 0.001, 0.01, 0.1, 1.0, 10.0, and 100.0 of DEAE-dextran to glucose oxidase, respectively. Four vials of control samples were prepared that contained 1 mL each of the working glucose oxidase solution with no working DEAE-dextran solution.

Each of the vials was capped, placed on a shaker trap to ensure mixing of the solution, frozen, and lyophilized over a period of several days to produce a powder in the vial. ETO sterilization was then carried out for a group of samples for about 1-hr (e.g., at an ETO gas dwell time of 1-hr) at a temperature of approximately 55 degrees C. and an average aeration time of 12 hours. A second group of samples was not subjected to ETO sterilization and maintained at room temperature. A third group of samples was not subjected to ETO sterilization and was frozen at −15 degrees C.

Following the sterilization procedure, each of the groups of samples were examined for biological activity as described in Example 1.

Figure 11:
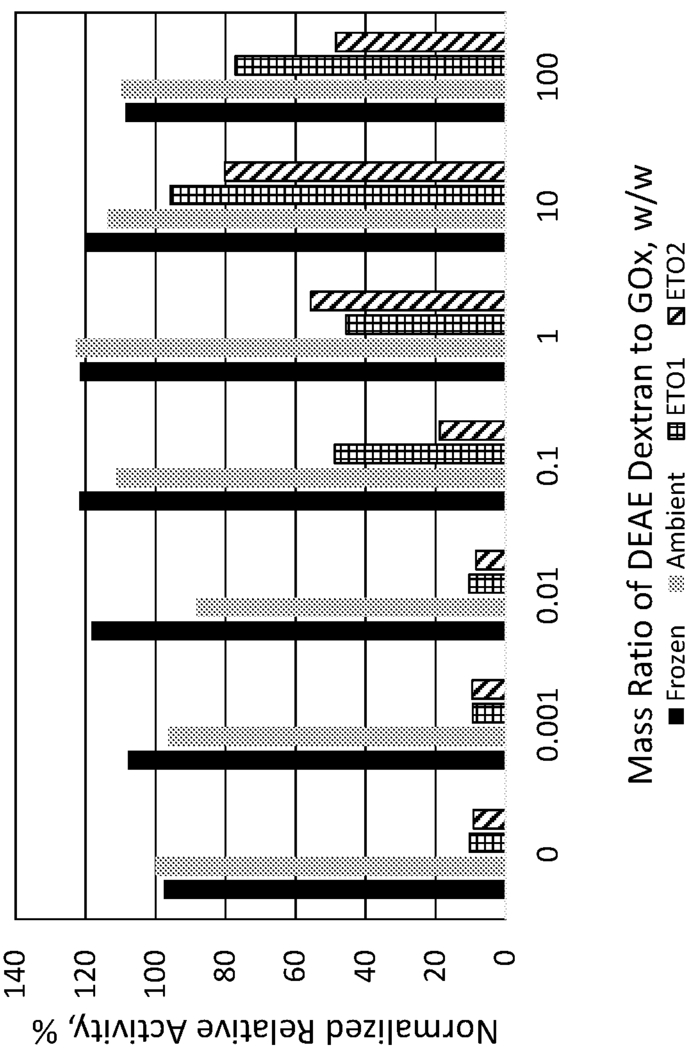
FIG. 11 is a graph showing the effect of diethylaminoethyl-dextran on glucose oxidase activity before and after ETO sterilization, in accordance with an embodiment.

FIG. 11 is a graph showing the effect of DEAE-dextran on glucose oxidase activity before and after ETO sterilization. The activity of glucose oxidase was expressed as normalized relative activity by dividing the measured activity for each sample by the measured value of a pure glucose oxidase control sample at room temperature and multiplying by 100 to yield a percentage. The pure glucose oxidase was obtained from the manufacturer's container and was not sterilized.

As shown in FIG. 11, sterilized glucose oxidase samples that received no DEAE-dextran showed a fairly large reduction in normalized relative activity compared to the control samples (e.g., samples that were not sterilized and were maintained at room temperature or frozen). The normalized relative activity of the room temperature control samples was 100%. The normalized relative activity of the frozen samples was 98%. The normalized relative activity of the sterilized samples that did not include DEAE-dextran was approximately 10% and 9%, respectively. Thus, it was concluded that ETO sterilization caused an approximate 90% reduction in biological activity of the glucose oxidase as compared to unsterilized samples.

The normalized relative activity of unsterilized samples treated with DEAE dextran, and maintained frozen at −15 C, showed an enhancement effect at a mass ratio of 0.01, 0.1, 1, and 10 as the normalized relative activity values were all above 117%. This effect was somewhat diminished at a mass ratio of 100 with an activity value of 108%. The room temperature samples showed an enhancement effect at a mass ratio of 0.1, 1, 10, and 100 with activity values of 111, 123, 113, and 110% respectively.

The sterilized samples having a mass ratio of 0.001 and 0.01 of DEAE-dextran to glucose oxidase showed little increase in biological activity as compared to the sterilized samples that did not include DEAE-dextran as all values were below 11%. An increase in retention of activity was observed for a mass ratio of DEAE dextran to GOx of 0.1 undergoing sterilization with all values above 15% as compared to the sterilized samples that did not include DEAE-dextran as all values were below 11%. The sterilized samples having a mass ratio of 10 and 100 of DEAE-dextran to glucose oxidase showed an increase in biological activity as compared to the sterilized samples that did not include DEAE-dextran. As shown, the biological activity of sterilized samples having a mass ratio of 10 and 100 ranged from about 45% to 95% and from about 48% to 80%, respectively. Thus, it was concluded that DEAE-dextran at mass ratios of about 10 to 100 of DEAE-dextran to glucose oxidase increases biological activity of the glucose oxidase after ETO sterilization as compared to samples having no DEAE-dextran. Further, these results demonstrated the ability to maintain the glucose activity of GOx following EtO sterilization with an appropriate biologically compatible composition non-covalently combined with GOx in powder form.

Example 5: Time Dependent Stability of a Stabilized Versus Non-Stabilized ePTFE Substrate A glucose stock solution of 1000 mg/dL was prepared by dissolving 4000 mg of D-(+)-glucose (Sigma-Aldrich, St. Louis, MO) into 40 ml of Dulbecco's Phosphate Buffered Saline (Sigma-Aldrich, St. Louis, MO). A working glucose solution of 100 mg/dL was made by diluting 10 mL of the stock solution to produce a final solution volume of 100 mL.

An ePTFE membrane [GORE™ Microfiltration Media (GMM-406), W. L. Gore & Associates, Inc., Flagstaff, AZ] with no immobilized glucose oxidase as a control was immersed in pure isopropyl alcohol to obtain a clear membrane that was wet out and placed in DI water for about 5 min. The ePTFE membrane was then placed over a tip of an Oakton WD-35643-12 dissolved oxygen meter. The tip was then placed into the working glucose solution and allowed to remain stationary. The percent dissolved oxygen meter recorded every 30 seconds for 3 minutes, then recorded again after 4 minutes, 6 minutes, and 8 minutes.

Figure 12:
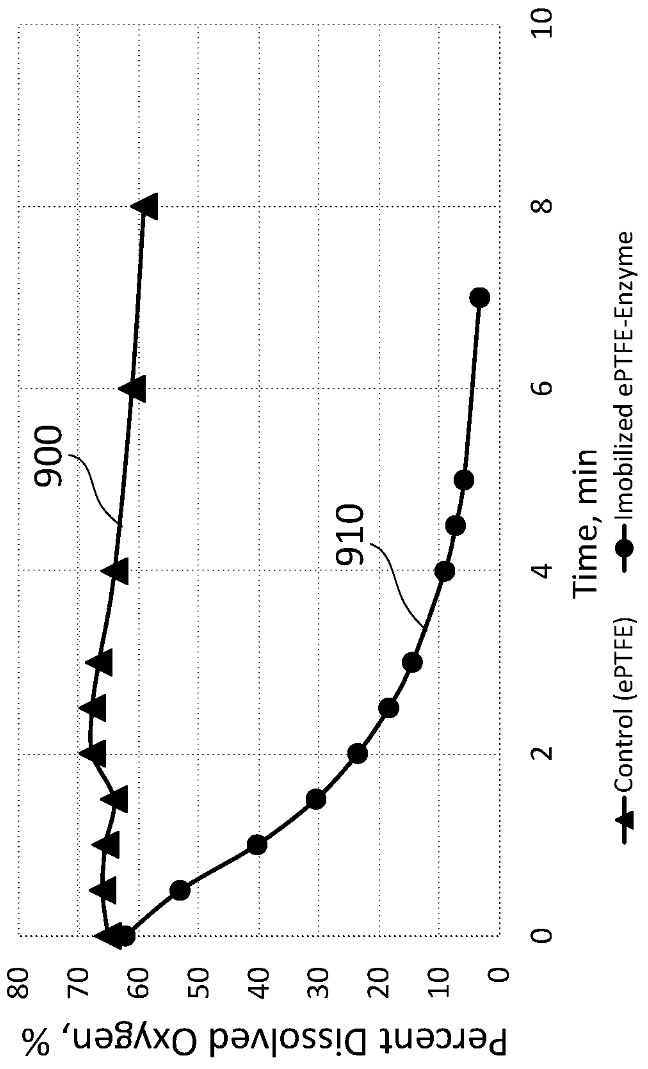
FIG. 12 is a graph showing time dependence of percent dissolved oxygen fora sensor tip positioned within a membrane, in accordance with an embodiment.

FIG. 12 shows the time dependent stability in percent dissolved oxygen for the oxygen probe fixed within the ePTFE membrane without immobilized glucose oxidase immersed in a glucose solution as shown in plot 900 of FIG. 12. As shown, over time, the percent dissolved oxygen varied from about 59% to 68% and shows no effect of ePTFE on dissolved oxygen levels. Therefore, no glucose oxidation occurred, which is indicative of low (or no) glucose oxidase activity.

An ePTFE membrane [GORE™ Microfiltration Media (GMM-406), W. L. Gore & Associates, Inc., Flagstaff, AZ] with stabilized glucose oxidase was prepared using the glucose stock solution as prepared above in this example. The membrane was mounted on a ten centimeter (10 cm) diameter plastic embroidery hoop and immersed first in 100% isopropyl alcohol (IPA) for about five minutes (5 min) and then in a PEI solution of LUPASOL® (LUPASOL® water-free Polyethylenimine, BASF Aktiengesellschaft, Germany) diluted with IPA in a one to one ratio (1:1) for about 15 minutes. The LUPASOL® water-free PEI was diluted to a concentration of about four percent (4%) and adjusted to pH 9.6 prior to addition of the IPA. Following immersion of the ePTFE material in the PEI solution for about fifteen minutes (15 min), the material was removed from the solution and rinsed in deionized (DI) water at pH 9.6 for fifteen minutes (15 min). PEI remaining on the ePTFE material was cross-linked with a 0.05% aqueous solution of glutaraldehyde (Amresco Inc., Solon, OH) at pH 9.6 for fifteen minutes (15 min). Additional PEI was added by placing the membrane in a 0.5% aqueous solution of PEI at pH 9.6 for fifteen minutes (15 min) and rinsing again in DI water at pH 9.6 for fifteen minutes (15 min). The imine formed as a result of the reaction between glutaraldehyde and the PEI layer is reduced with a sodium cyanoborohydride ($NaCNBH_3$) solution (5 g dissolved in 1 L DI water, pH 9.6) for fifteen minutes (15 min) and rinsed in DI water for thirty minutes (30 min).

A second layer of PEI was added by immersing the membrane in a 0.05% aqueous glutaraldehyde solution at pH 9.6 for fifteen minutes (15 min), followed by immersion in a 0.5% aqueous solution of PEI at pH 9.6 for fifteen minutes (15 min). The membrane was then rinsed in DI water at pH 9.6 for fifteen minutes (15 min). The resultant imines were reduced by immersing the membrane in a solution of $NaCNBH_3$ (5 g dissolved in 1 L DI water, pH 9.6) for fifteen minutes (15 min) followed by a rinse in DI water for thirty minutes (30 min).

A third layer of PEI was applied to the membrane by repeating the steps above. The resultant construction included a porous hydrophobic fluoropolymeric base material of ePTFE having a hydrophilic cross-linked polymer-based coating on substantially all of the exposed and interstitial surfaces of the fluoropolymeric base material.

An intermediate chemical layer was attached to the polymer base coat in preparation for placement of an additional layer of PEI on the construction. The intermediate ionic charge layer was made by incubating the construction in a solution of dextran sulfate (Amersham Pharmacia Biotech, UK) and sodium chloride (0.15 g dextran sulfate and 100 g NaCl dissolved in 1 L DI water, pH 3) at 60° C. for ninety minutes (90 min) followed by rinsing in DI water for fifteen minutes (15 min).

A "capping layer" of PEI was attached to the intermediate layer by placing the construction in a 0.3% aqueous solution of PEI (pH 9) for about forty-five minutes (45 min) followed by a rinse in a sodium chloride solution (50 g NaCl dissolved in 1 L DI water) for twenty minutes (20 min). A final DI water rinse was conducted for twenty minutes (20 min).

Glucose oxidase conjugation protocol in accordance with that described in G. T. Hermanson, *Bioconjugate Techniques, Third Edition,* 2013, was performed for glutaraldehyde crosslinking of amine particles with proteins such as glucose oxidase. Three samples of the above-described membranes were rinsed three times each in activation buffer (0.1 mM Sodium Phosphate Buffer, pH 7.0) and then samples were mixed at room temp in 0.5% glutaraldehyde in a coupling buffer (25 mM Sodium Phosphate Buffer, pH 7.0) for 1 hour. Samples were removed and placed in new containers and rinsed three times with coupling buffer. Glucose oxidase was added to samples at 0.01 mg/m L and mixed at room temperature for four hours. Ethanolamine was then added at a concentration of 0.2M for each sample to quench unreacted glutaraldehyde as samples were mixed at room temp for 30 minutes. Finally, samples were rinsed three times in coupling buffer, washed overnight in 2M Sodium Chloride, sonicated 15 minutes in 2% (w/v) Sodium Dodecyl Sulfate (SDS), and then left in coupling buffer in new containers prior to adding the stabilization molecules.

The ePTFE membrane was then placed over a tip of an Oakton WD-35643-12 dissolved oxygen meter. The tip was then placed into the working glucose solution and allowed to remain stationary. The percent dissolved oxygen meter recorded every 30 seconds for 5 minutes, then recorded again after 7 minutes.

FIG. 12 shows the time dependent stability in percent dissolved oxygen for the oxygen probe fixed within the ePTFE membrane with glucose oxidase as in plot 910 of FIG. 12. As shown, a reduction in the percent dissolved oxygen was observed after about 4 minutes, as the percent dissolved oxygen level declined from about 62% to 9%. Therefore, glucose oxidation occurred, which is indicative of high glucose oxidase activity due the reactants (e.g., glucose and oxygen) being readily consumed as the reaction occurs.

Example 6: PEI Coated ePTFE Conjugated with Glucose Oxidase

Coated constructions of ePTFE membrane [GORE™ Microfiltration Media (GMM-406), W.L. Gore & Associates, Inc., Flagstaff, AZ] were applied with a base coating of PEI and stabilized with glucose oxidase as prepared in accordance with Example 5.

Example 7: Constructions Treated with DEAE Dextran or Sorbose

The coated constructions according to Example 6 were exposed to solutions of the following compounds to evaluate their stabilizing effect on the activity of the glucose oxidase bound to the surface: DEAE dextran (10,000 molecular weight, PK Chemicals, Denmark) in DI water at concentrations of 0.05 g/ml, 0.005 g/ml, 0.0005 g/ml, 0.00005 g/ml, 0.000005 g/ml, and 0.0000005 g/ml and Sorbose (180.16 molecular weight, Sigma Aldrich, St. Louis, MO) in DI water at concentrations of 0.05 g/ml, 0.005 g/ml, 0.0005 g/ml, 0.00005 g/ml, 0.000005 g/ml, and 0.0000005 g/ml. Each of these solutions is referred to herein as a "treatment solution." The effect of these various concentrations on activity of glucose oxidase following EtO sterilization was expressed as UI/ml.

To expose a particular enzyme-containing construction to a particular treatment solution, sections of the construction were cut into 6 mm disks. Individual disks were placed in beakers and fifty microliters (50 ul) of treatment solution was added to each disk, sufficient to completely cover the construction in the treatment solution. Each construction was exposed to ambient conditions for one hour allowing ambient evaporation to remove the bulk of the solution. Samples were then lyophilized prior to exposure to a sterilization procedure.

Example 8: Effect of Mass Ratio of DEAE Dextran and Sorbose to Glucose Oxidase Non-Covalently Combined with GOx immobilized on an EPTFE Substrate Coated with PEI In preparation for EtO sterilization, each construction from Example 7 was placed and sealed in a Tower DUALPEEL® Self-Seal Pouch (Allegiance Healthcare Corp., McGaw Park, Ill.). Ethylene oxide sterilization was carried out under conditions of conditioning for one hour (1 hr), an EtO gas dwell time of three hours (3 hr), a set point temperature of forty-five degree centigrade (45° C.), and an aeration time of twelve hours (12 hr).

Figure 13:
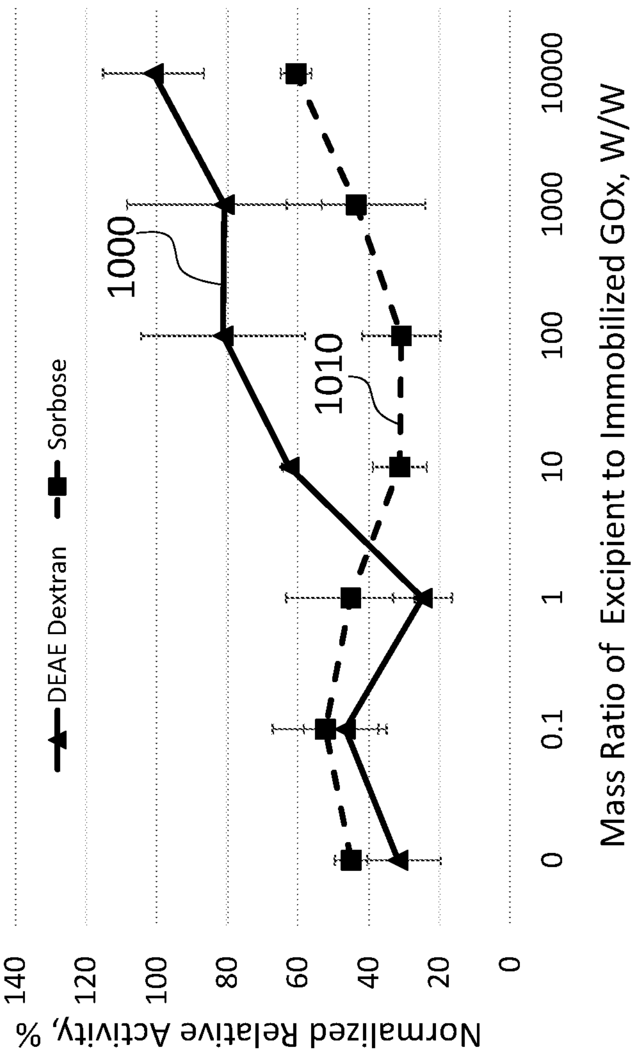
FIG. 13 is a graph showing the effect of glucose oxidase immobilization for an ePTFE substrate stabilized during ETO sterilization by admixing DEAE dextran and by admixing sorbose.

Data was collected for three samples each (n=3) generally. Due to sample failure, two samples each (n=2) generated data for the 10000 DEAE dextran and 1 Sorbose data as graphed on FIG. 13. As shown in FIG. 13, plot 1000 demonstrates that glucose oxidase immobilized on an ePTFE substrate can be stabilized for ETO sterilization by admixing DEAE dextran, specifically by immersing the substrate in DEAE dextran. As shown in FIG. 13, plot 1010 demonstrates that glucose oxidase immobilized on an ePTFE substrate can be stabilized for ETO sterilization by admixing sorbose, specifically be immersing the substrate in sorbose.

Enzyme Activity of each sample as a function of substrate volume was estimated by converting the mU/ml detected in the assay for the 6 mm discs of membrane in each test. The assay utilized 50 ul of solution for each sample. This represents the "true" enzyme activity per unit mass of substrate material. The sample volume for each disc was estimated as follows: 6 mm disc of approximately 34 μm in thickness and an effective void space of 0.87. This resulted in a sample volume of ePTFE of 0.000125 $cm^3$ for each disc (3 mm*3 mm*3.1415*0.034 mm/(1−0.87). Enzyme Activity for the samples is shown in Table 1 below.

TABLE 1

| | DEAE ($U/cm^3$) | | | | Sorbose ($U/cm^3$) | | | |
|---|---|---|---|---|---|---|---|---|
| Ratio | Non Sterile | Sterile Sample 1 | Sterile Sample 2 | Sterile Sample 3 | Non Sterile | Sterile Sample 1 | Sterile Sample 2 | Sterile Sample 3 |
| 0 | 116 | 131 | 62 | 84 | 208 | 146 | 128 | 120 |
| 0.1 | 270 | 98 | 164 | 146 | 267 | 102 | 180 | 175 |
| 1 | 201 | 98 | 50 | 69 | 339 | 94 | 169 | 0 |
| 10 | 375 | 189 | 179 | 179 | 319 | 115 | 86 | 72 |
| 100 | 271 | 301 | 166 | 243 | 388 | 121 | 91 | 57 |
| 1000 | 241 | 318 | 232 | 158 | 231 | 103 | 192 | 86 |
| 10000 | 339 | 324 | 265 | 79 | 352 | 165 | 175 | 190 |

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A stabilized medical device, comprising:

a substrate that is at least partially electrically conductive, and comprises electrically conductive expanded polytetrafluoroethylene (ePTFE);

a stabilized enzyme layer disposed over at least a portion of a surface of the substrate, the stabilized enzyme layer including:

at least one biologically active sensing component comprising glucose oxidase; and at least one stabilizing component non-covalently combined with the biologically active sensing component, wherein the stabilizing component is selected from the group consisting of: trehalose, diethylaminoethyl-dextran hydrochloride, and sorbose and wherein the biologically active sensing component is configured to sense a level of glucose G in a body of a patient, wherein the biologically active sensing component has a biological activity detection level from about 25 $U/cm^3$ to about 1,000,000 $U/cm^3$ of the substrate following ethylene oxide sterilization of the biologically active sensing component, wherein a mass ratio of the stabilizing component to the biologically active sensing component in the stabilized enzyme layer is from about 10 to about 50, and wherein the biologically active sensing component has a biological activity detection level after ethylene oxide sterilization that is within from about 40% to about 90% of a biological activity detection level before ethylene oxide sterilization.

2. The medical device of claim 1, wherein the biologically active sensing component has a biological activity detection level after ethylene oxide sterilization that is within from about 50% to about 80% of a biological activity detection level before ethylene oxide sterilization.

3. The medical device of claim 1, wherein the biologically active sensing component has a biological activity detection level from about 100 U/$cm^3$ to about 300 U/$cm^3$ of the substrate following ethylene oxide sterilization of the biologically active sensing component.

4. A method for making a stabilized medical device, the method comprising: mixing at least one stabilizing component selected from the group consisting of: trehalose, diethylaminoethyl-dextran hydrochloride, and sorbose with at least one sensing component comprising glucose oxidase to form a stabilized mixture, wherein the biologically active sensing component is configured to sense a level of glucose G in a body of a patient;

coating an electrically conductive substrate comprising electrically conductive expanded polytetrafluoroethylene (ePTFE) with the stabilized mixture to form a stabilized enzyme layer on at least a portion of the substrate; and subjecting the substrate to an ethylene oxide sterilization process, wherein a mass ratio of the stabilizing component to the biologically active sensing component in the stabilized enzyme layer is from about 10 to about 50, and wherein the biologically active sensing component has a biological activity detection level after ethylene oxide sterilization that is within from about 40% to about 90% of a biological activity detection level before ethylene oxide sterilization.

5. The method of claim 4, wherein the sensing component has a biological activity detection level from about 25 U/$cm^3$ to about 1,000,000 U/$cm^3$ of the substrate following ethylene oxide sterilization of the biologically active sensing component.

6. The method of claim 4, wherein the sensing component has biological activity detection level from about 100 U/$cm^3$ to about 300 U/$cm^3$ of the substrate following ethylene oxide sterilization of the biologically active sensing component.

* * * * *